United States Patent
Ito et al.

(10) Patent No.: US 6,723,319 B1
(45) Date of Patent: Apr. 20, 2004

(54) METHOD OF TREATING INFLAMMATORY INTESTINAL DISEASES CONTAINING AS THE INGREDIENT IL-6 RECEPTORS ANTIBODIES

(75) Inventors: Hiroaki Ito, Ashiya (JP); Mitsunari Yamamoto, Ibaraki (JP); Tadamitsu Kishimoto, 3-5-31, Nakano-cho, Tondabayashi-shi, Osaka 584-0021 (JP)

(73) Assignees: Chugai Seiyaku Kabushiki Kaisha, Tokyo (JP); Tadamitsu Kishimoto, Osaka (JP)

( * ) Notice: Subject to any disclaimer, the term of this patent is extended or adjusted under 35 U.S.C. 154(b) by 0 days.

(21) Appl. No.: 09/646,188
(22) PCT Filed: Mar. 16, 1999
(86) PCT No.: PCT/JP99/01298

§ 371 (c)(1),
(2), (4) Date: Sep. 14, 2000

(87) PCT Pub. No.: WO99/47170
PCT Pub. Date: Sep. 23, 1999

(30) Foreign Application Priority Data

Mar. 17, 1998 (JP) ............................................ 10-067250

(51) Int. Cl.⁷ ............................................ A61K 39/395
(52) U.S. Cl. ................................ 424/143.1; 424/130.1; 424/134.1; 424/139.1; 424/141.1; 424/142.1; 514/2; 514/8; 514/12
(58) Field of Search ........................... 514/2, 8, 12, 885; 530/387.1, 388.22, 388.23, 389.2; 435/375; 424/85.2, 134.1, 139.1, 141.1, 142.1, 143.1, 130.1

(56) References Cited

U.S. PATENT DOCUMENTS 5,888,510 A * 3/1999 Kishimoto et al. ...... 424/141.1

FOREIGN PATENT DOCUMENTS

| EP | 0 811 384 A1 | 12/1997 |
|---|---|---|
| JP | 7-324097 | 12/1995 |
| JP | 8-99996 | 4/1996 |
| JP | 8-245414 | 9/1996 |
| JP | 8-508299 | 9/1996 |
| JP | 8-311098 | 11/1996 |
| JP | 9-235276 | 9/1997 |
| WO | WO 96/38481 A1 | 12/1996 |
| WO | 96/40966 | 12/1996 |
| WO | WO 99/64069 A1 | 12/1999 |

OTHER PUBLICATIONS

Rogler G, Andus T. Cytokines in inflammatory bowel disease. World J Surg. 1998 Apr.;22(4):382–9. Review.*
Kmiec Z. Cytokines in inflammatory bowel disease. Arch Immunol Ther Exp (Warsz). 1998;46(3):143–55. Review.*
van Hogezand RA, Verspaget HW. Selective immunomodulation in patients with inflammatory bowel disease—future therapy or reality? Neth J Med. 1996 Feb;48(2):64–7. Review.*
Powrie et al., "Inhibition of Th1 Responses Prevents Inflammatory Bowel Disesas In scid Mice Reconstituted With CD45Rbhi CD4+ T Cells", *Immunity*, vol. 1:553–562, (1994).
Takagi et al., "Blockage Of Interleukin–6 Receptor Ameliorates Joint Disease In Murine Collagen–Induced Arthritis", *Arthritis $Reheumatism*, vol. 41(12):2117–2121, (1998).
Mitsuyama et al., "Soluble Interleukin–6 Receptors In Inflammatory Bowel Disease; Relation To Circulating Interleukin–6", *Gut*, vol. 36:45–49, (1995).
Van Dullemen et al., "Treatment Of Crohn's Disease With Anti–Tumor Necrosis Factor Chimeric Monoclonal Antibody (cA2)", *Gastroenterology*, vol. 109:129–135, (1995).
Sasajima et al., "Changes in Serum Cytokine Profile During Treatment of Ulcerative Colitis", *Journal of Gastroenterology and Hepatology*, Dec. 1997, p. A274, vol. 12, No. SUPPL. XP–001105732.
Funakoshi et al., "Spectrum of Cytokine Gene Expression in Intestinal Mucosal Lesions of Crohn's Disease and Ulcerativre Colitis", *Digestion*, Jan. 1998, pp. 73–78, vol. 59, No., Basel, China, XP–001064174.
Tateishi et al., "Role of Cytokines in Experimental Colitis: Relation to Intestinal Permeability", *Digestion*, 1997, pp. 271–281, vol. 58, No. 3, Basel, China, XP–001095980.
Seidman et al., "Nutritional Issues in Pediatric Inflammatory Bowel Disesase", *Journal of Pediatric Gastroenterology and Nutrition*, 1991, pp. 424–438, vol. 12, No. 4, Raven Press, Ltd., New York, XP–001105792.

* cited by examiner

*Primary Examiner*—Prema Mertz
(74) *Attorney, Agent, or Firm*—Foley & Lardner

(57) ABSTRACT

A preventive or therapeutic agent for treating bowel disease, including Crohn's disease and ulcerative colitis, where the agent has as an active ingredient an antibody directed against IL-6 receptor which is an interleukin-6 antagonist.

4 Claims, No Drawings

METHOD OF TREATING INFLAMMATORY INTESTINAL DISEASES CONTAINING AS THE INGREDIENT IL-6 RECEPTORS ANTIBODIES

TECHNICAL FIELD

The present invention relates to a preventive or therapeutic agent for inflammatory bowel disease comprising an interleukin-6 (IL-6) antagonist as an active ingredient. The present invention also relates to a preventive or therapeutic agent for Crohn's disease or ulcerative colitis comprising an IL-6 antagonist as an active ingredient.

BACKGROUND OF INVENTION

IL-6 is a cytokine which is also called B cell stimulating factor 2 (BSF2) or interferon β2. IL-6 was discovered as a differentiation factor involved in the activation of B-lymphocytic cells (Hirano, T. et al., Nature (1986) 324, 73–76). Thereafter, it was found to be a multifunctional cytokine that influences various functions of cells (Akira, S. et al., Adv. in Immunology (1993) 54, 1–78). IL-6 has been reported to induce the maturation of T-lymphocytic cells (Lotz, M. et al., J. Exp. Med. (1988) 167, 1253–1258).

IL-6 transmits its biological signal through two proteins on the cell. One of them is IL-6 receptor, a IL-6-binding protein with a molecular weight of about 80 kD, (Taga, T. et al., J. Exp. Med. (1987) 166, 967–981; Yamasaki, K. et al., Science (1987) 241, 825–828). IL-6 receptor exists not only in the membrane-bound form with transmembrane domain expressed on the cell surface but also as a soluble IL-6 receptor consisting mainly of the extracellular region.

The other is a membrane-bound protein gp130 having a molecular weight of about 130 kD that is involved in non-ligand-binding signal transduction. IL-6 and IL-6 receptor form the IL-6/IL-6 receptor complex, which after binding to gp130 transmits its biological signal to the cell (Taga, T. et al., Cell (1989) 58, 573–581).

IL-6 antagonists are substances that inhibit the transduction of biological activity of IL-6. As the IL-6 antagonists, there have been known so far antibody against IL-6 (anti-IL-6 antibody), antibody against IL-6 receptor (anti-IL-6 receptor antibody), and antibody against gp130 (anti-gp130 antibody), altered IL-6, partial peptides of IL-6 or IL-6 receptor and the like.

Anti-IL-6 receptor antibody has been described in several reports (Novick D. et al., Hybridoma (1991) 10, 137–146, Huang, Y. W. et al., Hybridoma (1993) 12, 621–630, International Patent Publication WO 95/09873, French Patent Application FR 2694767, U.S. Pat. No. 5,21,628). Humanized PM-1 antibody has been known that was obtained by grafting the complementarity determining region (CDR) of a mouse antibody PM-1 (Hirata, Y. et al., J. Immunology (1989) 143, 2900–2906) to a human template antibody (the International Patent Publication WO 92-19759).

Inflammatory bowel disease (IBD) is a nonspecific inflammation represented by ulcerative colitis and Crohn's disease. Immunological disturbances have been implicated in the onset of the disease, but that has not led to the elucidation of the etiology. It is believed, however, that monocytes and lymphocytes that clustered at lesion sites are involved in the damages of mucus, and inflammatory mediators, in particular cytokines (such as IL1β, TNFα, and IL-6) are drawing special attention.

For IL-6 among the inflammatory mediators, attention has been given to its relation to the disease status or to whether it could be an specific index for IBD. Serum level of IL-6 increases in both of Crohn's disease and ulcerative colitis, and the level correlates with the condition of the disease (Holtkamp, W. et al., J. Clin. Gastroenterology (1995) 20, 123–126, Niederau, C. et al., Hepato-Gastroenterology (1997) 44, 90–107). Measurement of amount of IL-6 mRNA in the tissue as PCR (polymerase chain reaction) products has revealed that it well correlated to the disease status of both ulcerative colitis and Crohn's disease (Stevens, C. et al., Dig. Dis. Sci. (1992) 37, 818–826). On the increase of IL-6 production during active IBD, the mechanism was analyzed and it was found that the amount of production when mononuclear cells in the lamina propria are stimulated by Pokeweed mitogen, are well correlated with the condition of disease (Reinecker, H.-C. et al., Clin. Exp. Immunol. (1993) 94, 174–181).

Thereafter, the correlation of IL-6 production and disease status was observed in the culture of mononuclear cells derived from the lamina propria and the tissue culture of the mucosa from patients. In the former case, it was also shown that the number of cells that produce IL-6 in the mucosal tissue also increased. Among the mononuclear cells the most important IL-6-producing cells are macrophage, and it has been confirmed that there are a great number of CD68-positive macrophages that vigorously produce IL-6 in the lamina propria of the IBD patients in the active stage (Kusugami, K. et al., Dig. Dis. Sci. (1995), 40, 949–959).

It has also been found that the production of IL-6 correlates to the endoscopic observation of patients with Crohn's disease (Reimund, J.-M. et al., Gut (1996) 39, 684–689). In addition, there are some reports that not only IL-6 but soluble IL-6 receptor concentration in serum well correlates with the disease status (Mitsuyama, K. et al., Gut (1995) 36, 45–49).

For inflammatory mediators other than IL-6, the amount of IL-1β production is also known to correlate to condition of disease. On the other hand, this is not always true for TNF-α and the amount of production may tend to be high in low activity in disease condition (Reinecker, H.-C. et al., Clin. Exp. Immunol. (1993) 94, 174–181, Reimund, J.-M. et al., Gut (1996) 39, 684–689).

The current method of treating IBD comprises a combination of diet and medication, with salazosulfapyridine, glucocorticoid, etc. being prescribed. For these drugs, however, there are intolerant patients due to their side effects, and thereby problems occur in terms of a long-term administration.

On the other hand, some trials are going on as a new treatment of IBD that intends to improve disease conditions through the inhibition of cytokine activity. Its main targets are IL-1 and TNF-α (Van Deventer, S. J. H. Gut (1997) 40, 443–448); for IL-1, an IL-1 receptor antagonist (Cominelli F. et al., Gastroenterology (1992) 103, 65–71) and an IL-1 inhibitor, CGP47969A (Casini-Raggi et al., Gastroenterology (1995) 109, 812–818), and the like are under study on the clinical or the experimental animal level. For TNF-α, specific monoclonal antibody has been administered to patients with Crohn's disease, in which reduced activity and cured ulcer have been observed (Van Dullemen, H. M. et al., Gastroenterology (1995) 109, 129–135). It was not known, however, that IL-6 antagonist can treat IBD to specifically suppress the biological activity of IL-6.

DISCLOSURE OF THE INVENTION

It is an object of the present invention to provide a preventive or therapeutic agent for inflammatory bowel disease said agent being free of the above-mentioned drawbacks.

Thus, the present invention provides (1) a preventive or therapeutic agent for inflammatory bowel disease comprising an IL-6 antagonist as an active ingredient.

The present invention also provides (2) a preventive or therapeutic agent for inflammatory bowel disease comprising an antibody against IL-6 receptor as an active ingredient.

The present invention also provides (3) a preventive or therapeutic agent for inflammatory bowel disease comprising a monoclonal antibody against IL-6 receptor as an active ingredient.

The present invention also provides (4) a preventive or therapeutic agent for inflammatory bowel disease comprising a monoclonal antibody against human IL-6 receptor as an active ingredient. The monoclonal antibody against human IL-6 receptor is preferably PM-1 antibody.

The present invention also provides (5) a preventive or therapeutic agent for inflammatory bowel disease comprising a monoclonal antibody against mouse IL-6 receptor as an active ingredient. The monoclonal antibody against mouse IL-6 receptor is preferably MR16-1 antibody.

The present invention also provides (6) a preventive or therapeutic agent for inflammatory bowel disease comprising a recombinant antibody against IL-6 receptor as an active ingredient. The recombinant antibody against IL-6 receptor has preferably a constant region (C region) of human antibody.

The present invention also provides (7) a preventive or therapeutic agent for inflammatory bowel disease comprising a chimeric or humanized antibody against IL-6 receptor as an active ingredient.

The present invention also provides (8) a preventive or therapeutic agent for inflammatory bowel disease comprising humanized PM-1 antibody as an active ingredient.

The present invention also provides (9) a preventive or therapeutic agent for Crohn's disease or ulcerative colitis comprising the IL-6 antagonist described in the above (1) to (8) as an active ingredient.

The present invention also provides (10) an agent for suppressing weight loss in inflammatory bowel disease said agent comprising the IL-6 antagonist described in the above (1) to (8) as an active ingredient.

The present invention also provides (11) an agent for suppressing weight loss in inflammatory bowel disease said agent comprising the IL-6 antagonist described in the above (3) to (8) as an active ingredient.

EMBODIMENT FOR CARRYING OUT THE INVENTION

IL-6 antagonists for use in the present invention may be of any origin, any kind, and any form, as long as they have a preventive or therapeutic effect on inflammatory bowel disease, or an effect of controlling weight loss in inflammatory bowel disease.

IL-6 antagonists block signal transduction by IL-6 and inhibit the biological activity of IL-6. As the IL-6 antagonists, there can be mentioned preferably anti-IL-6 antibody, anti-IL-6 receptor antibody, anti-gp130 antibody, altered IL-6, altered soluble IL-6 receptor, a partial peptide of IL-6 or IL-6 receptor, and a low molecular weight substances having the same activity as these.

Anti-IL-6 antibodies for use in the present invention can be obtained as polyclonal or monoclonal antibodies using a known method. As the anti-IL-6 antibodies for use in the present invention, monoclonal antibodies of, in particular, a mammalian origin, are preferred. Monoclonal antibodies of a mammalian origin include those produced by hybridomas and recombinant antibodies produced by host cell which has been transformed with an expression vector containing genetically engineered antibody genes. These antibodies, via binding to IL-6, block the binding of IL-6 to IL-6 receptor, and thereby blocks signal transduction of the biological activity of IL-6 into the cell.

Examples of such antibodies include MH166 (Matsuda et al., Eur. J. Immunol. (1988) 18, 951–956) and SK2 antibody (Sato, K. et al., The 21st Nihon Mennekigakkai Soukai (General Meeting of the Japan Immunology Society), Academic Record (1991) 21, 166) and the like.

An anti-IL-6 antibody-producing hybridoma can be basically constructed using a known procedure as described below. Thus, IL-6 may be used as a sensitizing antigen in the conventional method of immunization. The immunized cells thus obtained are fused with known parent cells in the conventional cell fusion process, and then monoclonal antibody-producing cells are screened by a conventional screening method to prepare the desired hybridoma.

Specifically, anti-IL-6 antibody may be obtained in the following manner. For example, a human IL-6 for use as a sensitizing antigen to obtain an antibody can be obtained using the IL-6 gene/amino acid sequence disclosed in Eur. J. Biochem (1987) 168, 543–550, J. Immuno. (1988) 140, 1534–1541, or Agr. Biol. Chem. (1990) 54, 2685–2688.

After a suitable host cell is transformed by inserting the IL-6 gene sequence into a known expression vector system, the IL-6 protein is purified from the host cell or the culture supernatant thereof. The purified IL-6 protein can be used as a sensitizing antigen. Alternatively, a fusion protein of the IL-6 protein and another protein may be used as a sensitizing antigen.

Anti-IL-6 receptor antibodies for use in the present invention can be obtained as polyclonal or monoclonal antibodies using a known method. As the anti-IL-6 antibodies for use in the present invention, monoclonal antibodies of, in particular, a mammalian origin, are preferred. Monoclonal antibodies of a mammalian origin include those produced by hybridomas and those produced by host cell which has been transformed with an expression vector containing genetically engineered antibody genes. The antibodies, via binding to IL-6 receptor, inhibit the binding of IL-6 to IL-6 receptor, and thereby block the transduction of the biological activity of IL-6 into the cell.

Examples of such antibodies include MR16-1 antibody (Tamura, T., et al., Proc. Natl. Acad. Sci. USA (1993) 90, 11924–11928), PM-1 antibody (Hirata, et al., J. Immunology (1989) 143, 2900–2906), or AUK12-20 antibody, AUK64-7 antibody or AUK146-15 antibody (International Patent Publication WO 92-19759), and the like. Among them, PM-1 antibody is most preferred.

The hybridoma cell line which produces PM-1 antibody has been internationally deposited under the provisions of the Budapest Treaty as PM-1 on Jul. 10, 1990 with the National Institute of Bioscience and Human Technology, Agency of Industrial Science and Technology, of 1-3, Higashi 1-chome, Tsukuba-shi, Ibaraki pref., Japan, as FERM BP-2998. In addition, the hybridoma cell line which produces MR16-1 antibody has been internationally deposited under the provisions of the Budapest Treaty as MR16-1 on Mar. 13, 1997 with the National Institute of Bioscience and Human Technology, Agency of Industrial Science and Technology, of 1-3, Higashi 1-chome, Tsukuba-shi, Ibaraki pref., Japan, as FERM BP-5875.

Hybridoma producing anti-IL-6 receptor monoclonal antibody can be basically constructed using a known procedure as described bellow. Thus, IL-6 receptor is used as a sensitizing antigen according to the conventional method of immunization. The immunized cells thus obtained are fused with known parent cells in a conventional cell fusion process, and then monoclonal antibody-producing cells may be screened by a conventional screening method to prepare a desired hybridoma.

Specifically, anti-IL-6 receptor antibody may be prepared in the following manner. For example, human IL-6 receptor used as a sensitizing antigen for obtaining an antibody can be obtained using the IL-6 receptor gene sequence/amino acid sequence disclosed in European Patent Application EP 325474, and mouse IL-6 receptor can be obtained using that disclosed in Japanese Unexamined Patent Publication (Kokai) 3(1991)-155795.

There are two types of IL-6 receptor proteins: IL-6 receptor expressed on the cell membrane, and IL-6 receptor detached from the cell membrane (soluble IL-6 Receptor) (Yasukawa, K. et al., J. Biochem. (1990) 108, 673–676). Soluble IL-6 receptor antibody consists essentially of an extracellular region of an IL-6 receptor bound to the cell membrane, and thereby is different from a membrane-bound IL-6 receptor in that the latter lacks the transmembrane region or both of the transmembrane region and the intracellular region. As the IL-6 receptor protein, any IL-6 receptor can be used, as long as it can be used a sensitizing antigen for production of the IL-6 receptor antibody for use in the present invention.

After a gene sequence of IL-6 receptor is inserted into a known expression vector system to transform an appropriate host cell, the desired IL-6 receptor protein may be purified from the host cells or a culture supernatant thereof using a known method. The IL-6 receptor protein thus purified may be used as a sensitizing antigen. Alternatively, cells that are expressing IL-6 receptor or a fusion protein of the IL-6 receptor protein and another protein may be used as a sensitizing antigen.

*E. coli* that has a plasmid pIBIBSF2R containing cDNA encoding human IL-6 receptor has been internationally deposited under the provisions of the Budapest Treaty as HB101-pIBIBSF2R on Jan. 9, 1989 with the National Institute of Bioscience and Human Technology, Agency of Industrial Science and Technology, of 1-3, Higashi 1-chome, Tsukuba-shi, Ibaraki pref., Japan, as FERM BP-2232.

Anti-gp130 antibodies for use in the present invention can be obtained as polyclonal or monoclonal antibodies using a known method. As the anti-gp130 antibodies for use in the present invention, monoclonal antibodies of, in particular, a mammalian origin, are preferred. Monoclonal antibodies of a mammalian origin include those produced by hybridomas and those produced by host cell which has been transformed with an expression vector containing genetically engineered antibody genes. The antibodies, via binding to gp130, inhibits the binding of IL-6/IL-6 receptor complex to gp130, and thereby blocks the transduction of the biological activity of IL-6 into the cell.

Examples of such antibodies include AM64 antibody (Japanese Unexamined Patent Publication (Kokai) 3(1991)-219894), 4B11 antibody and 2H4 antibody (U.S. Pat. No. 5,571,513), B-S12 antibody and B-P8 antibody (Japanese Unexamined Patent Publication (Kokai) 8(1996)-291199).

A monoclonal antibody-producing hybridoma can be basically created using a known procedure as described below. Thus, gp130 may be used as a sensitizing antigen and is used for immunization in a conventional method for immunization. The immunized cells thus obtained are fused with known parent cells in a conventional cell fusion process, and then monoclonal antibody-producing hybridomas are screened by a conventional screening method to prepare a desired hybridoma.

Specifically, monoclonal antibody may be obtained in the following manner. For example, gp130 used as a sensitizing antigen for antibody generation can be obtained using a gp130 gene sequence/amino acid sequence disclosed in European Patent Application EP 411946.

After inserting the gp130 gene sequence into a known expression vector system, a suitable host cell is transformed with the vector system, and the gp130 protein is purified from the host cell or from the culture supernatant thereof. The purified gp130 receptor protein can be used as the sensitizing antigen. Alternatively, a fusion protein of the gp130 protein and another protein may be used as a sensitizing antigen.

Though mammals to be immunized with a sensitizing antigen are not particularly limited, they are preferably selected in consideration of their compatibility with the parent cell for use in cell fusion. They generally include rodents such as mice, rats, hamsters and the like.

Immunization of animals with a sensitizing antigen is carried out using a known method. A general method, for example, involves an intraperitoneal or subcutaneous administration of a sensitizing antigen to a mammal. Specifically, a sensitizing antigen which has been diluted and suspended in an appropriate amount of phosphate buffered saline (PBS) or physiologic saline etc. is mixed, as desired, with an appropriate amount of a conventional adjuvant, for example Freund's complete adjuvant. After being emulsified, it is preferably administered to a mammal for several times every 4 to 21 days. Alternatively a suitable carrier may be used at the time of immunization with the sensitizing antigen.

After immunization and the confirmation of the increase in the desired antibody titer in the serum, the immunized cells are taken out from the mammal and are subjected to cell fusion. Preferred immunized cells include in particular the spleen cells.

The mammalian myeloma cells as the other parent cells which are subjected to cell fusion with the above-mentioned immune cells preferably include various known cell lines such as P3X63Ag8.653) (Kearney, J. F. et al., J. Immunol. (1979) 123: 1548–1550), P3X63Ag8U.1 (Current Topics in Microbiology and Immunology (1978) 81: 1–7), NS-1 (Kohler, G. and Milstein, C., Eur. J. Immunol. (1976) 6: 511–519), MPC-11 (Margulies, D. H. et al., Cell (1976) 8: 405–415), SP2/0 (Shulman, M. et al., Nature (1978) 276: 269–270), FO (de St. Groth, S. F. et al., J. Immunol. Methods (1980) 35: 1–21), S194 (Trowbridge, I. S., J. Exp. Med. (1978) 148: 313–323), R210 (Galfre, G. et al., Nature (1979) 277: 131–133) and the like.

Cell fusion between the above immunized cells and the myeloma cells may be essentially conducted in accordance with a known method such as is described in Milstein et al. (Kohler, G. and Milstein, C., Methods Enzymol. (1981) 73: 3–46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used. In addition, an adjuvant such as dimethyl sulfoxide etc. may be added as desired to enhance the efficiency of fusion.

The preferred ratio of the immunized cells and the myeloma cells to be used is, for example, 1 to 10 times more immunized cells than the myeloma cells. Examples of culture media to be used for the above cell fusion include RPMI1640 medium and MEM culture medium suitable for the growth of the above myeloma cell lines, and the conventional culture medium used for this type of cell culture, and a serum supplement such as fetal calf serum (FCS) may be added.

In cell fusion, designated amounts of the above immunized cells and the myeloma cells are mixed well in the above culture medium, to which a PEG solution previously heated to about 37° C., for example a PEG solution with a mean molecular weight of about 1000 to 6000, is added at a concentration of 30 to 60% (w/v) and mixed to obtain the desired fusion cells (hybridomas). Then by repeating the sequential addition of a suitable culture medium and centrifugation to remove the supernatant, cell fusion agents etc. which are undesirable for the growth of the hybridoma can be removed.

Said hybridoma is selected by culture in a conventional selection medium, for example, HAT medium (a culture medium containing hypoxanthine, aminopterin, and thymidine). Culturing in HAT medium is continued generally for a period of time sufficient to effect killing of the cells other than the desired hybridoma (non-fusion cells), generally several days to several weeks. The conventional limiting dilution method is conducted in which the hybridomas that produce the desired antibody are screened and cloned.

In addition to obtaining the above hybridoma by immunizing an animal other than human with an antigen, it is also possible to sensitize human lymphocytes in vitro with a desired antigen or desired antigen-expressing cells, and the resulting sensitized B lymphocytes are fused with a human myeloma cell, for example U266, to obtain a desired human antibody having the activity of binding to desired antigen or desired antigen-expressing cells (see Japanese Post-examined Patent Publication (Kokoku) 1(1989)-59878). Furthermore, a transgenic animal having a repertoire of all human antibody genes is immunized with an antigen or an antigen-expressing cells to obtain a desired human antibody in the method described above (see International Patent Publication WO 93/12227, WO 92/03918, WO 94/02602, WO 94/25585, WO 96/34096 and WO 96/33735).

The monoclonal antibody-producing hybridomas thus constructed can be subcultured in a conventional culture medium, or can be stored for a prolonged period of time in liquid nitrogen.

In order to obtain monoclonal antibodies from said hybridoma, a method can be used in which said hybridoma is cultured in a conventional method and an antibody is obtained in a supernatant, or a method in which the hybridoma is administered to and grown in a mammal compatible with said hybridoma and an antibody is obtained in the ascites. The former method is suitable for obtaining high-purity antibodies, whereas the latter is suitable for a large scale production of antibodies.

Specifically a hybridoma producing anti-IL-6 receptor antibody can be constructed using the method disclosed in Japanese Unexamined Patent Publication (Kokai) 3(1989)-139293. It can be conducted by a method in which the PM-1 antibody-producing hybridoma that was internationally deposited under the provisions of the Budapest Treaty as FERM BP-2998 on Jul. 10, 1990 with the National Institute of Bioscience and Human Technology, Agency of Industrial Science and Technology, of 1-3, Higashi 1-chome, Tsukuba-shi, Ibaraki pref., Japan, is intraperitoneally injected to BALB/c mice to obtain the ascites from which the PM-1 antibody is purified, or a method in which said hybridoma is cultured in a suitable culture medium such as RPMI1640 medium containing 10% fetal bovine serum and 5% BM-Condimed H1 (manufactured by Boehringer Mannheim), the hybridoma SFM medium (manufactured by GIBCO-BRL), the PFHM-II medium (manufactured by GIBCO-BRL) and the like, and the PM-1 antibody can be purified from the supernatant.

A recombinant antibody which was produced by a gene recombination technology, in which an antibody gene was cloned from the hybridoma and integrated into a suitable vector, which transformed host cells, can be used in the present invention as monoclonal antibody (see, for example, Borrebaeck C. A. K., and Larrick J. W. THERAPEUTIC MONOCLONAL ANTIBODIES, published in the United Kingdom by MACMILLAN PUBLISHERS LTD. 1990).

Specifically, mRNA encoding a variable region (V) of a desired antibody is isolated from antibody-producing cells such as a hybridoma. The isolation of mRNA is conducted by preparing total RNA using, for example, a known method such as the guanidine ultracentrifuge method (Chirgwin, J. M. et al., Biochemistry (1979) 18, 5294–5299), the AGPC method (Chomczynski, P. et al., Anal. Biochem. (1987) 162, 156–159), and then mRNA is purified from the total RNA using the mRNA Purification kit (manufactured by Pharmacia) and the like. Alternatively, mRNA can be directly prepared using the Quick Prep mRNA Purification Kit (manufactured by Pharmacia).

cDNA of a V region of an antibody may be synthesized from the mRNA using a reverse transcriptase. cDNA may be synthesized using an AMV Reverse Transcriptase First-strand cDNA Synthesis Kit and the like. Alternatively, for the synthesis and amplification of CDNA, a 5'-Ampli FINDER RACE Kit (manufactured by Clontech) and a 5'-RACE method (Frohman, M. A. et al., Proc. Natl. Acad. Sci. USA (1988) 85, 8998–9002; Belyavsky, A. et al., Nucleic Acids Res. (1989) 17, 2919–2932) that employs polymerase chain reaction (PCR) may be used. A desired DNA fragment is purified from the PCR product obtained and may be ligated to vector DNA. Moreover, a recombinant vector is constructed therefrom and then is transformed into E. coli etc., from which colonies are selected to prepare a desired recombinant vector. The nucleotide sequence of a desired DNA may be confirmed by a known method such as the dideoxy method.

Once the DNA encoding a V region of a desired antibody has been obtained, it may be ligated to DNA encoding a constant region (C region) of a desired antibody, which is then integrated into an expression vector. Alternatively, a DNA encoding a V region of an antibody may be integrated into an expression vector which already contains DNA encoding a C region of an antibody.

In order to produce an antibody for use in the present invention, an antibody gene is integrated as described below into an expression vector so as to be expressed under the control of an expression regulatory region, for example an enhancer and/or a promoter. Subsequently, the expression vector may be transformed into a host cell and the antibody can then be expressed therein.

In accordance with the present invention, artificially altered recombinant antibody such as chimeric antibody and humanized antibody can be used for the purpose of lowering heterologous antigenicity against humans. These altered antibody can be produced using known methods.

Chimeric antibody can be obtained by ligating the thus obtained DNA encoding a V region of antibody to a DNA encoding a C region of a human antibody, which is then integrated into an expression vector and transformed into host cell for production of the antibody therein (see European Patent Application EP 125023, and International Patent Publication WO 92/19759). Using this known method, useful chimeric antibody for the present invention can be obtained.

For example, the plasmid that contains DNA encoding the L chain V region or the H chain V region of chimeric PM-1 antibody was designated as pPM-k3 or pPM-h1, respectively, and *E. coli* having the plasmid has been internationally deposited under the provisions of the Budapest Treaty as NCIMB 40366 and NCIMB 40362, respectively, on Feb. 11, 1991 with the National Collections of Industrial and Marine Bacteria Limited.

Humanized antibody which is also called reshaped human antibody has been made by grafting the complementarity determining regions (CDRs) of an antibody of a mammal other than the human, for example mouse antibody, into CDRs of a human antibody. The general recombinant DNA technology for preparation of such antibodies is also known (see European Patent Application EP 125023 and International Patent Publication WO 92-19759).

Specifically, a DNA sequence which was designed to ligate the CDRs of a mouse antibody with the framework regions (FRs) of a human antibody is synthesized from several divided oligonucleotides having sections overlapping with one another at the ends thereof. The DNA thus obtained is ligated to the DNA encoding the C region of human antibody and then is integrated into an expression vector, which is transformed into host cells for antibody production (see European Patent Application EP 239400 and International Patent Publication WO 92-19759).

For the FRs of a human antibody ligated to CDR, the complementarity determining region that forms a favorable antigen binding structure is selected. When desired, amino acids in the framework region of the antibody variable region may be substituted so that the complementarity determining region of reshaped human antibody may form an appropriate antigen binding structure (Sato, K. et al., Cancer Res. (1993) 53, 851–856).

For example, for chimeric antibody or humanized antibody, a C region of human antibody is used. As the C region of human antibody, there can be mentioned Cγ, and Cγ1, Cγ2, Cγ3, and Cγ4, for example, can be used. The C region of human antibody may be modified to improve the stability of antibody or the production thereof.

Chimeric antibody consists of the variable region of antibody derived from a mammal other than the human and the C region derived from human antibody, whereas humanized antibody consists of the complementarity determining regions of an antibody derived from a mammal other than the human and the framework regions and the C region of antibody derived from a human antibody. Accordingly, antigenicity thereof in the human body has been reduced so that they are useful as antibodies for use in the present invention.

A preferred embodiment of the humanized antibody for use in the present invention includes humanized PM-1 antibody (see International Patent Publication WO 92-19759).

Antibody genes constructed as described above may be expressed and the product is obtained in known methods. In the case of mammalian cells, expression may be accomplished using a vector containing a conventionally used useful promoter, the antibody gene to be expressed, and DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for expression of antibody for use in the present invention, there are viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Mulligan, R. C. et al., Nature (1979) 277, 108–114) when SV40 promoter/enhancer is used, or by the method of Mizushima et al. (Mizushima, S. and Nagata, S. Nucleic Acids Res. (1990) 18, 5322) when HEF1α promoter/enhancer is used.

In the case of *E. coli*, expression may be conducted by operably linking a conventionally used useful promoter, a signal sequence for antibody secretion, and an antibody gene to be expressed, followed by expression thereof. As the promoter, for example, there can be mentioned lacz promoter and araB promoter. The method of Ward et al. (Ward, E. S. et al., Nature (1989) 341, 544–546; Ward, E. S. et al., FASEB J. (1992) 6, 2422–2427) may be used when lacz promoter is used, and the method of Better et al. (Better, M. et al., Science (1988) 240, 1041–1043) may be used when araB promoter is used.

As the signal sequence for antibody secretion, when produced in the periplasm of *E. coli*, the pelB signal sequence (Lei, S. P. et al., J. Bacteriol. (1987) 169, 4379–4383) can be used. After separating the antibody accumulated in the periplasm, the structure of the antibody is appropriately refolded before use (see, for example, WO 96/30394).

As an origin of replication, there can be used those derived from SV40, polyoma virus, adenovirus, bovine papilloma virus (BPV) and the like. Furthermore, for the amplification of the gene copy number in the host cell system, expression vectors can include as selectable markers an aminoglycoside phospho transferase (APH) gene, a thymidine kinase (TK) gene, *E. coli* xanthine guaninephosphoribosyl transferase (Ecogpt) gene, a dihydrofolate reductase (dhfr) gene and the like.

For the production of antibody for use in the present invention, any production system can be used. The production system of antibody preparation comprises the in vitro or the in vivo production system. As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as Xenopus oocytes, or (3) insect cells such as sf9, sf21, and Tn5. Known plant cells include, for example, those derived from *Nicotiana tabacum*, which may be subjected to callus culture. Known fungal cells include yeasts such as the genus Saccharomyces, more specifically *Saccharomyces cereviceae*, or filamentous fungi such as the genus Aspergillus, more specifically *Aspergillus niger*.

When prokaryotic cells are used, there are the production systems which employ bacterial cells. Known bacterial cells include *Escherichia coli* (*E. coli*), and *Bacillus subtilis*.

By transformation a gene for a desired antibody into these cells and culturing the transformed cells in vitro, the antibody can be obtained. Culturing is conducted in the known methods. For example, as the culture medium, DMEM, MEM, RPMI1640, and IMDM can be used, and serum supplements such as fetal calf serum (FCS) may be used in combination. In addition, antibodies may be produced in vivo by injection of cells transformed by antibody gene into the abdominal cavity of an animal and the like.

As in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also as insects, silkworms can be used.

When plants are used, tabacco, for example, can be used.

Antibody genes are transformed into these animals or plants, and the antibodies are produced in such animals or plants, and recovered. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is transferred into a female goat. The desired antibody is obtained from the milk produced by the transgenic goat borne to the goat who received the embryo or the offspring thereof. In order to increase the amount of milk containing the desired antibody produced by the transgenic goat, hormones may be given to the transgenic goat as appropriate. (Ebert, K. M. et al., Bio/Technology (1994) 12, 699–702).

When silkworms are used, baculovirus into which a desired antibody gene has been inserted is infected to the silkworm, and the desired antibody can be obtained from the body fluid of the silkworm (Maeda, S. et al., Nature (1985) 315, 592–594). Moreover, when tabacco is used, the desired antibody gene is inserted into an expression vector for plants, for example pMON 530, and then the vector is infected to a bacterium such as *Agrobacterium tumefaciens*. The bacterium is then infected to tabacco such as *Nicotiana tabacum* to obtain the desired antibody from the leaves of the tabacco (Julian, K.-C. Ma et al., Eur. J. Immunol. (1994) 24, 131–138).

When antibody is produced in vitro or in vivo production systems, as described above, DNA encoding the heavy chain (H chain) or the light chain (L chain) of antibody may be separately integrated into an each expression vector and the hosts are transformed simultaneously, or DNA encoding the H chain and the L chain may be integrated into a single expression vector and a host is transformed therewith (see International Patent Publication WO 94-11523).

Antibodies for use in the present invention may be antibody fragments or modified versions thereof as long as they are preferably used. For example, as fragments of antibody, there may be mentioned Fab, F(ab')2, Fv or single-chain Fv (scFv) in which Fv's of H chain and L chain were ligated via a suitable linker.

Specifically antibodies are treated with an enzyme, for example, papain or pepsin, to produce antibody fragments, or genes encoding these antibody fragments are constructed, and then integrated into an expression vector, which is expressed in a suitable host cell (see, for example, Co, M. S. et al., J. Immunol. (1994) 152, 2968–2976; Better, M. and Horwitz, A. H., Methods in Enzymology (1989) 178, 476–496; Plueckthun, A. and Skerra, A., Methods in Enzymology (1989) 178, 476–496; Lamoyi, E., Methods in Enzymology (1986) 121, 652–663; Rousseaux, J. et al., Methods in Enzymology (1986) 121, 663–669; Bird, R. E. et al., TIBTECH (1991) 9, 132–137).

scFv can be obtained by ligating the V region of H chain and the V region of L chain of antibody. In the scFv, the V region of H chain and the V region of L chain are preferably ligated via a linker, preferably a peptide linker (Huston, J. S. et al., Proc. Natl. Acad. Sci. USA (1988) 85, 5879–5883). The V region of H chain and the V region of L chain in the scFv may be derived from any of the above-mentioned antibodies. As the peptide linker for ligating the V regions, any single-chain peptide comprising, for example, 12–19 amino acid residues may be used.

DNA encoding scFv can be obtained using DNA encoding the H chain or the H chain V region of the above antibody and DNA encoding the L chain or the L chain V region of the above antibody as the template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA be ligated to the H chain and the L chain, respectively.

Once DNAs encoding scFv are constructed, an expression vector containing them and a host transformed with said expression vector can be obtained by the conventional methods, and scFv can be obtained using the transformed host by the conventional methods.

These antibody fragments can be produced by obtaining the gene thereof in a similar manner to that mentioned above and by allowing it to be expressed in a host. "Antibody" as used in the claim of the present application encompasses these antibody fragments.

As modified antibodies, antibodies associated with various molecules such as polyethylene glycol (PEG) can be used. "Antibody" as used in the claim of the present application encompasses these modified antibodies. These modified antibodies can be obtained by chemically modifying the antibodies thus obtained. These methods have already been established in the art.

Antibodies produced and expressed as described above can be separated from the inside or outside of the host cell and then may be purified to homogeneity. Separation and purification of the antibody for use in the present invention may be accomplished by affinity chromatography. As the column used for such affinity chromatography, there can be mentioned Protein A column and Protein G column. Examples of the carriers used in the Protein A column are Hyper D, POROS, Sepharose F. F. and the like. Alternatively, methods for separation and purification conventionally used for proteins can be used without any limitation. Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like. These chromatographies can be applied into high performance liquid chromatography (HPLC). Alternatively, reverse-phase HPLC can be used.

The concentration of antibody obtained in the above can be determined by the measurement of absorbance or by the enzyme-linked immunosorbent assay (ELISA) and the like. Thus, when absorbance measurement is employed, a sample is appropriately diluted with PBS(−) and then the absorbance is measured at 280 nm, followed by calculation using the absorption coefficient of 1.35 OD at 1 mg/ml. When the ELISA method is used, measurement is conducted as follows. Thus, 100 μl of goat anti-human IgG (manufactured by TAGO) diluted to 1 μg/ml in 0.1 M bicarbonate buffer, pH 9.6, is added to a 96-well plate (manufactured by Nunc), and is incubated overnight at 4° C. to immobilize the antibody. After blocking, 100 μl each of appropriately diluted antibody of the present invention or a sample containing the antibody, or 100 μl of human IgG (manufactured by CAPPEL) as the standard is added, and incubated at room temperature for 1 hour.

After washing, 100 μl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

The altered IL-6 for use in the present invention has an activity of binding to IL-6 receptor and does not transmit the biological activity of IL-6. Thus, the altered IL-6, though it competes with IL-6 for binding to IL-6 receptor, does not transmit the biological activity of IL-6, and thereby it blocks signal transduction by IL-6.

Altered IL-6 may be constructed through the introduction of mutation by replacing amino acid residues of the amino acid sequence of IL-6. IL-6, the source of the altered IL-6, may be of any origin, but when the antigenicity is to be considered, it is preferably human IL-6.

Specifically, the secondary structure of IL-6 is predicted using a known molecular modeling program of the amino acid sequence, for example WHATIF (Vriend et al., J. Mol. Graphics (1990), 8, 52–56), and the overall effects on the amino acid residue to be replaced is evaluated. After an appropriate amino acid residue was determined, mutation is introduced by the conventionally used polymerase chain reaction (PCR) method using a vector containing the nucleotide sequence encoding human IL-6 gene thereby to obtain a gene encoding altered IL-6. This is then integrated, as desired, into an appropriate expression vector, from which altered IL-6 can be obtained according to the expression, production and purification of said recombinant antibody.

Specific examples of the altered IL-6 are disclosed in Brakenhoff et al., J. Biol. Chem. (1994) 269, 86–93, and Savino et al., EMBO J. (1994) 13, 1357–1367, WO 96-18648, and WO 96-17869.

The partial peptides of IL-6 or IL-6 receptor for use in the present invention have an activity of binding to IL-6 receptor or IL-6, respectively, and does not transmit the biological activity of IL-6. Thus, the partial peptides of IL-6 or IL-6 receptor bind to IL-6 receptor or IL-6, respectively, and thereby capture it. As a result, they do not transmit the biological activity of IL-6, and block signal transduction of IL-6.

The partial peptides of IL-6 or the IL-6 receptor are peptides comprising some or all of the amino acid sequence of the region involved in the binding to IL-6 and IL-6 receptor in the amino acid sequence of IL-6 or IL-6 receptor. Such peptides generally comprises 10–80, preferably 20–50, more preferably 20–40 amino acid residues.

The partial peptides of IL-6 or the IL-6 receptor can be constructed by specifying the region involved in the binding to IL-6 and IL-6 receptor in the amino acid sequence of IL-6 or IL-6 receptor, and by producing some or all of the amino acid sequence by a conventional method such as a genetic engineering technology or a peptide synthesis method.

In order to produce the partial peptides of IL-6 or IL-6 receptor by a genetic engineering technology, the DNA sequence encoding the desired peptide is integrated into an expression vector, from which the peptide can be obtained by the expression, production, and purification of said recombinant antibody.

Production of the partial peptide of IL-6 or IL-6 receptor by the peptide synthesis method can be effected using a method commonly used in peptide synthesis such as the solid phase synthesis or the liquid phase synthesis.

Specifically the method described in Zoku-Iyakuhin no Kaihatsu (Sequel to Development of Pharmaceuticals), Vol. 14, Peputido Gousei (Peptide Synthesis), edited by Haruaki Yajima, Hirokawa Shoten, 1991, may be used. The solid phase synthesis method used includes, for example, a reaction in which an amino acid corresponding to the C-terminal of the peptide to be synthesized is coupled to a support which is insoluble in organic solvents, and then an amino acid in which α-amino group or a side chain functional group has been protected with an appropriate protecting group is condensed one amino acid at a time from the C-terminal to the N-terminal direction, and a reaction in which said protecting group of the α-amino group of the amino acid or the peptide coupled to the resin is eliminated is alternately repeated to elongate the peptide chain. The solid phase peptide synthesis methods are divided into the Boc method and the Fmoc method depending on the type of protecting group to be used.

After the synthesis of the desired peptide is complete, a deprotection reaction and a reaction for cleaving the peptide chain from the support is carried out. For cleavage from the peptide chain, hydrogen fluoride or trifuluoromethane-sulfonic acid in the Boc method and TFA in the Fmoc method are generally used. In the Boc method, for example, the above peptide resin is treated in hydrogen fluoride in the presence of anisole. Subsequently, the protecting group is eliminated and the peptide is recovered by cleaving from the support. By lyophilizing this, crude peptide can be obtained. On the other hand, in the Fmoc method, TFA, for example, is used in a manner similar to the above to effect the deprotection reaction and the cleavage reaction of the peptide from the support.

The crude peptide thus obtained can be applied to HPLC for its separation and purification. Its elution can be carried out in a water-acetonitrile solvent system that is commonly used for protein purification under an optimum condition. The fraction corresponding to the peak of the profile of the chromatography obtained is collected and lyophilized. The peptide fraction thus purified is identified by subjecting it to the analysis of molecular weight by mass spectroscopy, the analysis of amino acid composition, or the analysis of amino acid sequence, and the like.

Specific examples of the IL-6 partial peptide or the IL-6 receptor partial peptide are disclosed in Japanese Unexamined Patent Publication (Kokai) 2(1990)-188600, Japanese Unexamined Patent Publication (Kokai) 7(1995)-324097, Japanese Unexamined Patent Publication (Kokai) 8(1996)-311098, and U.S. Pat. No. 5,210,075.

The activity of the IL-6 antagonist for use in the present invention can be evaluated using a conventionally known method. Specifically, the IL-6-dependent cell MH60.BSF2 is cultured, to which IL-6 is added, and the activity can be evaluated using the incorporation of $^3$H-thymidine into the IL-6-dependent cell in the coexistence of the IL-6 antagonist. Alternatively, evaluation can be effected by culture of U266, a IL-6 receptor-expressing cell, adding thereto $^{125}$I-labeled IL-6 and an IL-6 antagonist at the same time, and then by determining the $^{125}$I-labeled IL-6 bound to the IL-6 receptor-expressing cell. In the above assay system, a negative control group containing no IL-6 antagonists, in addition to the group in which an IL-6 receptor antagonist is present, is set up, and the results obtained for them are compared to evaluate the IL-6-inhibiting activity of the IL-6 receptor antagonist.

In order to confirm the effects accomplished by the present invention, an IL-6 antagonist for use in the present invention is administered to animals that developed inflammatory bowel disease by the injection of CD4-positive and CD45RB-strong positive cells (CD4$^+$CD45RB$^{high}$ cells), and the effect of suppressing weight loss and of improving the inflammatory bowel disease score can be evaluated. As additional effects of the present invention, there are effects of suppressing anorexia, reducing abdominal pains, ameliorating diarrhea, or preventing recurrence of inflammatory bowel disease.

The CD4$^+$CD45RB$^{high}$ cells that are transferred into animals by an IL-6 antagonist may be isolated by using, for example, the method described in the Example below. Animals from which CD4$^+$CD45RB$^{high}$ cells are derived may be those commonly used in experiments such as mice and rats.

As described in the Example below, in the animals that developed inflammatory bowel disease, the administration of IL-6 receptor antibody resulted in suppression of weight loss and improvement in the inflammatory bowel disease score, and thus it was revealed that IL-6 antagonists such as anti-IL-6 receptor antibody exert a therapeutic effect on inflammatory bowel disease.

The subject to be treated in the present invention is mammals. The subject to be treated is preferably humans.

The preventive or therapeutic agents of the present invention may be administered, either orally or parenterally, systemically or locally. For example, intravenous injection such as drip infusion, intramuscular injection, intraperitoneal injection, subcutaneous injection, suppositories, intestinal lavage, oral enteric coated tablets, and the like can be selected, and the method of administration may be chosen, as appropriate, depending on the age and the conditions of the patient. The effective dosage is chosen from the range of 0.01 mg to 100 mg per kg of body weight per administration. Alternatively, the dosage in the range of 1 to 1000 mg, preferably 5 to 50 mg per patient may be chosen.

The preventive or therapeutic agents for inflammatory bowel disease of the present invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, sodium carboxymethylcellulose, polyacrylic sodium, sodium alginate, water-soluble dextran, sodium carboxymethyl starch, pectin, methyl cellulose, ethyl cellulose, xanthan gum, Arabic gum, casein, gelatin, agar, diglycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof depending on the dosage form.

The subject disease to be treated of the present invention is inflammatory bowel disease. Inflammatory bowel disease includes ulcerative colitis and Crohn's disease. These diseases occur mostly in young people about 20 years of age, and little is known, even today, about the causative antigens or the mechanism of inflammatory pathology. However, extensive research is under way to elucidate them with various cells and cytokines.

In the last few years, progress has been observed in the analysis of cells that cause inflammatory bowel disease. Thus, it has become apparent that the animal model of inflammatory bowel disease can be constructed by transfer of purified CD4-positive, CD45RB-strong positive cells (CD4$^+$CD45RB$^{high}$) to immunodeficient mice (SCID mice) (Morrissey, P. J. et al., J. Exp. Med. (1993) 178, 237–244; Leach, M. W. et al., Am. J. Pathol. (1996) 148, 1503–1515; Aranda, R. et al., J. Immunol. (1997) 158, 3464–3473).

On the other hand, it has been shown that CD4-positive, CD45RB-weak positive cells (CD4$^+$CD45RB$^{low}$) cannot induce inflammatory bowel disease, and it rather suppresses the induction of inflammatory bowel disease by CD4-positive, CD45RB-strong positive cells (Powrie, F. R. et al., J. Exp. Med. (1994) 179, 589–600). The amount of CD45RB expression per cell is known to correlate to the cytokine production pattern. Thus, it is believed that CD4-positive, CD45RB-strong positive cells are type 1 helper (Th1)-like cells that produce IFN-γ and TNF-α, whereas CD4-positive, CD45RB-weak positive cells are type 2 helper cells (Th2)-like that produce IL-4, IL-10, and the like (Lee, W. et al., J. Immunol. (1990) 144, 3288–3295).

Thus, it is thought that the onset of IBD is most probably associated with the disturbed balance of Th1 and Th2, and this has been endorsed by the fact that chronic enteritis resembling human ulcerative colitis developed in IL-10 deficient mouse that was made by the gene targeting method (Kuhn, R. et al. Cell (1993) 75, 263–274).

Model animals used in the Example are very similar to patients with ulcerative colitis and Crohn's disease in the histoloical features of the colon (Leach, M. W. et al., Am. J. Pathol. (1996) 148, 1503–1515). In ulcerative colitis, lesions are often seen in extensive succession from the rectum and the epithelia of mucosa are specifically injured. In the present model, clinical pathologies are very similar in that the injured sites covers a wide area, though mainly localized in colon, and crypt extends.

On the other hand, Crohn's disease is a full thickness inflammation, not localized in the mucosa, and is disseminated in anywhere in the alimentary canal from the oral cavity to the anus. Histologically, it is characterised by inflammation of noncaseating granuloma. This model is very similar to Crohn's disease in that inflammation not localized in the mucosal layer is found, where macrophage, lymphocytes, and multinuclear giant cells accumulate, and often takes the form of granuloma, and that crypt abscess is seldom found.

Thus, cases in which the features of ulcerative colitis and Crohn's disease coexist have been reported so far in the clinical research (Tanaka, M. et al, Hepato-gastroenterology (1990) 37, 18–31). In inflammatory bowel disease, enhanced expression of the major histocompatibility complex class II is found in the epithelium (Trejdosiewicz, L. K. et al., Dig. Dis. Sci. (1989) 34, 1449–1456), and the same holds true for the present model. In this model, characteristic thickening of the epithielial tissue appears, which is believed to be associated with enhanced cellular growth found in patients with ulcerative colitis (Serafini, E. P. et al., Gut (1981) 22, 648–652).

The present model is very similar to clinical inflammatory bowel disease, and may induce weight loss in severe cases.

In an experiment using the present model, histological damages were markedly ameliorated and weight loss was not observed, which indicates that an IL-6 antagonist exhibits a therapeutic effect on inflammatory bowel disease such as ulcerative colitis or Crohn's disease.

EXAMPLES

The present invention will now be explained in more detail. It should be noted, however, that the present invention is not limited to them in any way.

Example

The spleen was aseptically removed from male BALB/c mice, and after homogenization, it was well pipetted to make a suspension of single cells. Then, in order to remove red blood cells, the cell pellet was treated with the lysis solution (a 9:1 mixture of 0.16 M $NH_4Cl$ and 0.17 M Tris buffer, pH 7.2), which was further washed twice with phosphate buffered saline to obtain mouse spleen cells.

The washed mouse spleen cells were suspended into an RPMI1640 medium containing 2% FCS, and after cell counting, it was adjusted to $1.1 \times 10^8$/ml. To this was added anti-mouse CD4 antibody (L3T4 Microbeads, manufactured by Miltenyi Biotec) at a 1/5 volume and was bound to the cells on ice for 15 minutes (at a cell density of $1 \times 10^8$/ml). Furthermore, by a column operation using the Mini MACS separation system (manufactured by Miltenyi Biotec), the CD4-positive cell fraction were collected. After cell counting, it was suspended in a 2% FCS-added phosphate buffered saline to adjust the cell density at $4 \times 10^7$/ml.

To a suspension of CD4-positive cells were added 1/100 volume of PE-labeled rat anti-mouse CD4 (L3T4) antibody (0.2 mg/ml, clone RM4-5, manufactured by Pharmingen) and 1/100 volume of FITC-labeled rat anti-mouse CD45RB antibody (0.5 mg/ml, clone 16A, manufactured by Pharmingen). By allowing this to stand on ice for 20 minutes, antibody was bound thereto. To the labeled cells was added a 2% FCS-added RPMI1640 medium, which was washed by centrifugation, and was resuspended in a 2% FCS-added phosphate buffered saline and stored at a cold dark place.

From the labeled CD4-positive cells, cells of the CD4-positive and CD45RB-strong positive cell ($CD4^+$ $CD45RB^{high}$ cells) group were selected-using a flow cytometer (FACS Vantage, manufactured by Becton Dickinson). This cell group corresponds to the upper 50% of the cells having a high expression of CD45RB among the CD4- and CD45RB-positive cells. The cells obtained, after centrifugation, was suspended in phosphate buffered saline to a concentration of $4 \times 10^6$/ml. The purity of the cells was 97% as the CD45RB-positive cells, and the survival rate thereof was 98%.

This highly purified cells was injected intraperitoneally at $4 \times 10^5$/ml (100 µl each of $4 \times 10^6$/ml) to C.B-17 scid mice to prepare the inflammatory bowel disease model (Leach, M. W. et al., Am. J. Pathol. (1996) 148, 1503–1515, Aranda, R. et al., J. Immunol. (1997) 158, 3464–3473). The experiment was performed for the following three groups by the treatment method: (1) the cell transfer, anti-IL-6 receptor antibody non-administration group, 5 mice, (2) the cell transfer, anti-IL-6 receptor antibody administration group, 3 mice, and (3) the cell non-transfer group, 3 mice.

Anti-IL-6 receptor antibody MR16-1 was given as follows. First, it was adjusted to 20 mg/ml in phosphate buffered saline, 100 µl per mouse of which was intraperitoneally given 15 to 30 minutes before injection of the above cells. One week later, it was adjusted to 10 mg/ml in phosphate buffered saline, 100 µl per mouse of which was intraperitoneally given. This was repeated every week until the 8th week after the cell transfer. The antibody non-administration group received phosphate buffered saline in a similar manner.

Mice 8 to 9 weeks after the cell transfer were weighed, and then the colon tissue (the descending colon portion) was removed and immersed in the OCT compound. Samples were frozen at $-80°$ C. Using a cryostat, these sample blocks were sliced to a frozen section of 6 µm in thickness, which was fixed in a 10% formalin solution. The fixed section was double-stained in the hematoxylin-eosin method for histological analysis.

The evaluation of drug efficacy was carried out by determining changes in body weight (ratio of before and after the cell transfer) and histological analysis before the induction of inflammatory bowel disease by the cell transfer and 8–9 weeks after the cell transfer. For histological analysis, the tissue of each mouse was assessed based on the following 4 stages of inflammatory bowel disease score (hereinafter referred to as the bowel disease score) (Ito, H. et al., J. Autoimmunity (1997) 10, 455–459).

Inflammatory bowel disease score:

Grade 0 (non): indistinguishable from the normal BALB/c mice,

Grade 1 (minimal): a slight hypertrophy of epithelial tissues observed,

Grade 2 (moderate): an intermediate of Grade 1 and 3,

Grade 3 (severe): a marked hypertrophy of epithelial tissues accompanied by a wide spread inflammatory cell infiltration and goblet cell deficiency.

The results on body weight change inflammatory bowel disease score were shown in Table 1.

The mice that were implanted the CD4-positive and CD45RB-strong positive cells developed inflammatory bowel disease and marked inflammation was also observed histologically. They have also shown debility associated with the onset of the disease, and 11% decrease in average body weight. On the other hand, in the anti-IL-6 receptor antibody administration group, statistically significant suppression of weight loss was observed, and about the same body weight as before the cell transfer was retained. Furthermore, histological inflammatory bowel disease scores have shown the amelioration of inflammatory bowel disease as well.

For the statistical test of changes in body weight, ANOVA (Analysis of variance, SPSS for windows ver. 6, SPSS Inc.) was first carried out to confirm significance followed by a multiple comparison by the Bonferroni method, in which significance was observed with a significance level of 5%.

This model is very similar to human inflammatory bowel disease, and thus it was demonstrated that anti-IL-6 receptor antibody is effective as a preventive or therapeutic agent for inflammatory bowel disease such as ulcerative colitis or Crohn's disease.

TABLE 1

Suppression of weight loss and bowel disease aggravation by anti-IL-6 receptor antibody

| Injected cell | Treatment | Number of animals | Changes in body weight (%) | Bowel disease score |
|---|---|---|---|---|
| CD4+CD45RBhigh | Phosphate buffered saline | 5 | 88.8 ± 6.7 | 2.4 |
| CD4+CD45RBhigh | Anti-IL-6 receptor antibody | 3 | 100.9 ± 4.5 | 1.0 |
| None | Phosphate buffered saline | 3 | 107.7 ± 0.9 | 0.3 |

Change in body weight was expressed as the mean±standard deviation of the group.

The bowel disease score was expressed as the mean of the group.

Example 2

Preparation of Human Soluble IL-6 Receptor

Soluble IL-6 receptor was prepared by the PCR method using a plasmid pBSF2R.236 containing cDNA that encodes IL-6 receptor obtained according to the method of Yamasaki et al., (Yamasaki, K. et al., Science (1988) 241, 825–828). Plasmid pBSF2R.236 was digested with a restriction enzyme Sph I to obtain the cDNA of IL-6 receptor, which was then inserted into mp18 (manufactured by Amersham). Using a synthetic oligoprimer designed to insert a stop codon into the cDNA of IL-6 receptor, a mutation was occurred in the cDNA of IL-6 receptor by the PCR method using the in vitro Mutagenesis System (manufactured by Amersham). The procedure resulted in the insertion of a stop codon to the amino acid at position 345, and gave CDNA encoding soluble IL-6 receptor.

In order to express the CDNA of soluble IL-6 receptor in CHO cells, it was ligated to plasmid pSV (manufactured by Pharmacia) to obtain plasmid pSVL344. The cDNA of soluble IL-6 receptor that was cleaved with Hind III-Sal I was inserted to plasmid pECEdhfr containing the cDNA of dhfr to obtain plasmid pECEdhfr344 that can be expressed in the CHO cells.

Ten µg of plasmid pECEdhfr344 was transfected to a dhfr-CHO cell line DXB-11 (Urland et al., Proc. Natl. Acad. Sci. USA (1980) 77, 4216–4220) by the calcium phosphate precipitation method (Chen C. et al., Mol. Cell. Biol. (1987) 7, 2745–2751). The transfected CHO cells were cultured for 3 weeks in a nucleoside-free a MEM selection medium containing 1 mM glutamine, 10% dialyzed FCS, 100 U/ml penicillin, and 100 µg/ml streptomycin.

The selected CHO cells were screened by the limiting dilution method to obtain a single CHO cell clone. The CHO cell clone was amplified in 20 nM–200 nM methotrexate (MTX) to obtain a CHO cell line 5E27 that produces human soluble IL-6 receptor. The CHO cell line 5E27 was cultured in an Iscov-modified Dulbecco's medium (IMDM, manufactured by Gibco) containing 5% FBS. The culture supernatant was collected and the concentration of soluble IL-6 receptor in the culture supernatant was determined by ELISA. The result confirmed that soluble IL-6 receptor is present in the culture supernatant.

Example 3

Preparation of Human IL-6 Antibody

Ten µg of the recombinant IL-6 (Hirano et al., Immunol. Lett., 17:41, 1988) was immunized to BALB/c mice together with Freund's complete adjuvant, and this was repeated every week until anti-IL-6 antibody could be detected in the serum. Immune cells were removed from local lymph node and were then fused with a myeloma cell line P3U1 using polyethylene glycol 1500. Hybridomas were selected according to the method of Oi et al. (Selective Methods in Cellular Immunolgy, W.H. Freeman and Co., San Francisco, 351, 1980) that employs the HAT medium, and the hybridoma that produces human IL-6 antibody was established.

The hybridoma that produces human IL-6 antibody was subjected to IL-6 binding assay as follows. Thus, a 96-well microtiter plate made of flexible polyvinyl (manufactured by Dynatech Laboratories, Inc., Alexandria, Va.) was coated with 100 µl of goat anti-mouse Ig (10 µl/ml, manufactured by Cooper Biomedical, Inc., Malvern, Pa.) overnight at 4° C. Subsequently, the plate was treated with PBS containing 1% bovine serum albumin (BSA) at room temperature for 2 hours.

After washing it in PBS, 100 µl of the hybridoma culture supernatant was added to each well, and then was incubated overnight at 4° C. The plate was washed, $^{125}$I-labeled recombinant IL-6 was added to each well to a concentration of 2000 cpm/0.5 ng/well, and then the radioactivity of each well after washing was determined by a gamma counter (Beckman Gamma 9000, Beckman Instruments, Fullerton, Calif.). Of 216 hybridoma clones, 32 were positive in the IL-6 binding assay. From these clones, stable MH166.BSF2 was finally obtained. Anti-IL-6 antibody MH166 produced by said hybridoma has a subtype of IgG1 κ.

Then, the IL-6-dependent mouse hybridoma clone MH60.BSF2 was used to examine a neutralizing activity with respect to the growth of the hybridoma by MH166 antibody. MH60.BSF2 cells were dispensed to $1 \times 10^4/200$ µl/well, and samples containing MH166 antibody were added thereto, cultured for 48 hours, 0.5 µCi/well of $^3$H-thymidine (New England Nuclear, Boston, Mass.) was added, and the culture was continued for further 6 hours. The cells were placed on a glass filter paper and were treated by the automatic harvester (Labo Mash Science Co., Tokyo, Japan). As the control, rabbit anti-IL-6 antibody was used.

As a result, MH166 antibody inhibited, in a dose dependent manner, the incorporation of $^3$H-thymidine of MH60.BSF2 cells induced by IL-6. This revealed that MH166 antibody neutralizes the activity of IL-6.

Example 4

Preparation of Human Anti-IL-6 Receptor Antibody

Anti-IL-6 receptor antibody MT18 prepared by the method of Hirata et al. (Hirata, Y. et al. J. Immunol., 143, 2900–2906, 1989) was bound to CNBr-activated Sepharose 4B (manufactured by Pharmacia Fine Chemicals, Piscataway, N.J.) according to the attached regimen, and IL-6 receptor (Yamasaki, K. et al., Science (1988) 241, 825–828) was purified. A human myeloma cell line U266 was solubilized with 1 mM p-para-aminophenyl methane sulfonyl fluoride hydrochloride (manufactured by Wako Chemicals) containing 1% digitonin (manufactured by Wako Chemicals), 10 mM triethanolamine (pH 7.8) and 0.15 M NaCl (digitonin buffer), and mixed with MT18 antibody bound to Sepharose 4B beads. Then, the beads were washed six times with the digitonin buffer to prepare the partially purified IL-6 receptor.

BALB/c mice were immunized four times every ten days with the above partially purified IL-6 receptor obtained from $3 \times 10^9$ U266 cells, and then a hybridoma was prepared using a standard method. The hybridoma culture supernatant from the growth-positive well was tested for its activity of binding to IL-6 receptor according to the method described below. $5 \times 10^7$ U266 cells were labeled with $^{35}$S-methionine (2.5 mCi) and were solubilized with the above digitonin buffer. The solubilized U266 cells were mixed with a 0.04 ml of MT18 antibody bound to Sepharose 4B beads, and then were washed six times with the digitonin buffer. $^{35}$S-methionine-labeled IL-6 receptor was eluted with 0.25 ml of the digitonin buffer (pH 3.4) and was neutralized in 0.025 ml of 1M Tris (pH 7.4).

0.05 ml of the hybridoma culture supernatant was mixed with 0.01 ml of Protein G Sepharose (manufactured by Pharmacia). After washing, Sepharose was incubated with 0.005 ml $^{35}$S-labeled IL-6 receptor solution prepared as described above. The immunoprecipitate was analyzed by SDS-PAGE to search the hybridoma culture supernatant that reacts with IL-6 receptor. As a result, the -positive hybridoma clone PM-1 was established. The antibody produced from the hybridoma PM-1 has a subtype of IgGκ.

The inhibitory activity of the antibody produced by the hybridoma PM-1 against binding of IL-6 to human IL-6 receptor was studied using the human myeloma cell line U266. A human recombinant IL-6 was prepared from *E. coli* (Hirano et al., Immunol. Lett., 17:41–45, 1988), and was labeled with $^{125}$I using the Bolton-Hunter reagent (New England Nuclear, Boston, Mass.) (Taga, T. et al., J. Exp. Med. (1987) 166, 967–981). $4 \times 10^5$ U266 cells were cultured with the 70% (v/v) of culture supernatant of hybridoma PM-1 together with 14,000 cpm of $^{125}$I-labeled IL-6 one hour at room temperature. Seventy µl of the sample was layered on 300 µl FCS in a 400 µl microfuge polyethylene tube. After centrifugation, the radioactivity of the cell was determined.

The result revealed that the antibody produced by the hybridoma PM-1 inhibits the binding of IL-6 to IL-6 receptor.

Example 5

Preparation of Mouse Anti-IL-6 Receptor Antibody

A monoclonal antibody against mouse IL-6 receptor was prepared according to the method described in Saito, et al., J. Immunol. (1993) 147, 168–173.

The CHO cells that produce mouse soluble IL-6 receptor were cultured in the IMDM medium containing 10% FCS. From the culture supernatant, mouse soluble IL-6 receptor was purified using mouse soluble IL-6 receptor antibody RS12 (see Saito, et al., supra) and an affinity column fixed to Affigel 10 gel (manufactured by Biorad).

The mouse soluble IL-6 receptor (50 µg) was mixed with Freund's complete adjuvant, which was then injected to the abdominal cavity of Wistar rats. From 2 weeks after the administration, the animals were boosted with Freund's incomplete adjuvant. On day 45, the rats were sacrificed, and the spleen cells at about $2 \times 10^8$ were fused with $1 \times 10^7$ mouse myeloma cells P3U1 using a 50% PEG1500 (Boehringer Mannheim) according to the conventional method, and then were screened by the HAT culture medium.

After the culture supernatants of hybridomas were added to the plate coated with rabbit anti-rat IgG antibody (manufactured by Cappel), mouse soluble IL-6 receptor was added. Subsequently, using rabbit anti-mouse IL-6 receptor antibody and alkaline phosphatase-labeled sheep anti-rabbit IgG, hybridomas producing anti-mouse soluble IL-6 receptor antibody were screened by ELISA. After production of desired antibody was confirmed, the hybridoma clones were subscreened twice to obtain a single hybridoma clone. The clone was designated as MR16-1.

The neutralizing activity of the antibody produced by the hybridoma on signal transduction of mouse IL-6 was examined by $^3$H-thymidine incorporation using MH60.BSF2 cells (Matsuda, T. et al., J. Immunol. (1988) 18, 951–956). MH60.BSF2 cells were prepared at $1 \times 10^4$ cells/200 µl/well in 96-well-microplate. 10 pg/ml mouse IL-6 and MR16-1 antibody or RS12 antibody at 12.3–1000 ng/ml were added to each well, and then were cultured at 37° C. for 44 hours in 5% $CO_2$ condition and then 1 µCi/well of $^3$H-thymidine was added. After 4 hours, the incorporation of $^3$H-thymidine was measured. As a result, MR16-1 antibody suppressed the incorporation of $^3$H-thymidine of the MH60.BSF2 cells.

Thus, it was demonstrated that the antibody produced by the hybridoma MR16-1 inhibits the binding of IL-6 to IL-6 receptor.

INDUSTRIAL APPLICABILITY

In accordance with the present invention, it was shown that an IL-6 antagonist such as anti-IL-6 receptor antibody has a therapeutic effect on inflammatory bowel disease. Thus, it was demonstrated that an IL-6 antagonist is useful as a therapeutic agent for Crohn's disease or ulcerative colitis.

What is claimed is:

1. A method of treating inflammatory bowel disease, said method comprising administering an anti-interleukin-6 receptor antibody, wherein the antibody used is the monoclonal antibody, PM-1 against human IL-6 receptor.

2. A method of treating inflammatory bowel disease, said method comprising administering an anti-interleukin-6 receptor antibody, wherein the antibody used is the monoclonal antibody MR16-1 against human IL-6 receptor.

3. A method of treating inflammatory bowel disease according to claim 1 or 2, wherein the inflammatory bowel disease is Crohn's disease or ulcerative colitis.

4. The method according to claim 1, wherein the monoclonal antibody PM-1 is a humanized antibody.

* * * * *

UNITED STATES PATENT AND TRADEMARK OFFICE
CERTIFICATE OF CORRECTION

PATENT NO. : 6,723,319 B1
DATED : April 20, 2004
INVENTOR(S) : Hiroaki Ito, Mitsunari Yamamoto and Tadamitsu Kishimoto It is certified that error appears in the above-identified patent and that said Letters Patent is hereby corrected as shown below:

Column 22,
Line 49, change "human IL-6" to -- mouse IL-6 --.

Signed and Sealed this

Fourteenth Day of September, 2004

JON W. DUDAS
*Director of the United States Patent and Trademark Office*